United States Patent [19]

Richter et al.

[11] 4,012,222

[45] * Mar. 15, 1977

[54] HERBICIDAL COMPOSITIONS CONTAINING DIOXOLANE SUBSTITUTED ANILIDS AND METHOD THEREFOR

[75] Inventors: Sidney B. Richter, Chicago; John Krenzer, Oak Park, both of Ill.

[73] Assignee: Velsicol Chemical Corporation, Chicago, Ill.

[ * ] Notice: The portion of the term of this patent subsequent to Jan. 7, 1992, has been disclaimed.

[22] Filed: Jan. 5, 1976

[21] Appl. No.: 646,719

Related U.S. Application Data

[62] Division of Ser. No. 523,388, Nov. 13, 1974, Pat. No. 3,946,045.

[52] U.S. Cl. .................................................. 71/88
[51] Int. Cl.² ......................................... A01N 9/00
[58] Field of Search ........................................ 71/88

[56] References Cited

UNITED STATES PATENTS

| | | | |
|---|---|---|---|
| 3,547,620 | 12/1970 | Olin | 71/88 X |
| 3,630,716 | 12/1971 | Olin | 71/88 X |
| 3,859,308 | 1/1975 | Richter et al. | 71/88 X |
| 3,888,882 | 6/1975 | Richter et al. | 71/88 X |
| 3,940,259 | 2/1976 | Richter et al. | 71/88 |
| 3,942,972 | 3/1976 | Richter et al. | 71/88 |
| 3,946,044 | 3/1976 | Richter et al. | 71/88 X |
| 3,948,950 | 4/1976 | Richter et al. | 71/88 X |

*Primary Examiner*—Joseph Paul Brust
*Attorney, Agent, or Firm*—Robert J. Schwarz; Dietmar H. Olesch

[57] ABSTRACT

This invention discloses new compounds of the formula

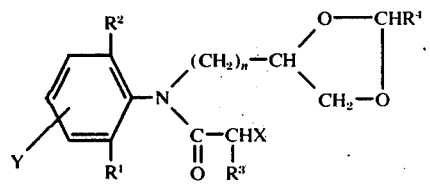

wherein Y is selected from the group consisting of hydrogen, lower alkyl and halogen; $R^1$ is selected from the group consisting of hydrogen, lower alkyl and lower alkoxy; $R^2$ is lower alkyl; $R^3$ and $R^4$ are independently selected from the group consisting of hydrogen and lower alkyl; X is halogen; and $n$ is the integer 1 or 2. The compounds of the above description are useful as herbicides.

9 Claims, No Drawings

HERBICIDAL COMPOSITIONS CONTAINING DIOXOLANE SUBSTITUTED ANILIDS AND METHOD THEREFOR

This application is a division of copending application Ser. No. 523,388, filed Nov. 13, 1974, now U.S. Pat. No. 3,946,045, issued Mar. 23, 1976.

This invention relates to new compositions of matter and more specifically relates to new compounds of the formula

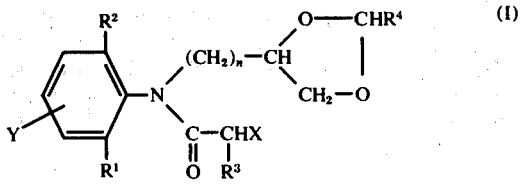

wherein Y is selected from the group consisting of hydrogen, lower alkyl and halogen; $R^1$ is selected from the group consisting of hydrogen, lower alkyl and lower alkoxy; $R^2$ is lower alkyl; $R^3$ and $R^4$ are independently selected from the group consisting of hydrogen and lower alkyl; X is halogen; and $n$ is the integer 1 or 2.

The term lower as used herein designates a straight or branched carbon chain of up to and including 6 carbon atoms.

The compounds of the present invention are unexpectedly useful as herbicides and are particularly useful in controlling grassy weeds.

In a preferred embodiment of the present invention Y is hydrogen and X is chlorine or bromine.

The compounds of the present invention can be prepared by reacting a compound of the formula

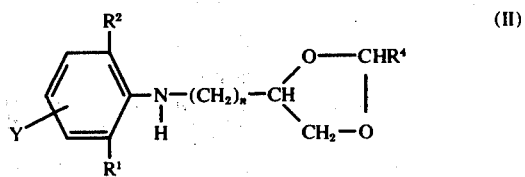

wherein Y, $R^1$, $R^2$, $R^4$ and $n$ are as heretofore described, with an α-haloalkanoyl chloride of the formula

wherein $R^3$ and X are as heretofore described. This reaction can be effected by combining a compound of formula II with a compound of formula III in an inert organic reaction medium, such as dioxane or benzene, in the presence of an acid acceptor, such as an alkali metal carbonate or bicarbonate, at a temperature of from about $-10°$ C to about $25°$ C and stirring the resulting mixture for a period of from about 15 to about 120 minutes. The reaction mixture can then be heated at temperatures ranging up to the reflux temperature of the reaction mixture to ensure completion of the reaction. After this time the reaction mixture can be washed with water to remove inorganic salts and stripped of solvent to yield the desired product. This product can be used as such or can be further purified by conventional techniques.

The compounds of formula II can be prepared by reacting a substituted aniline of the formula

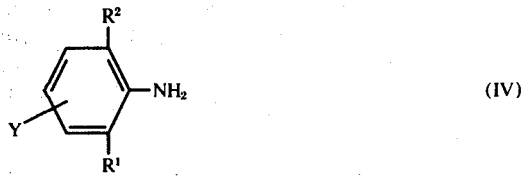

wherein Y, $R^1$ and $R^2$ are as heretofore described, with a compound of the formula

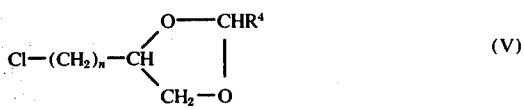

wherein $R^4$ and $n$ are as heretofore described. This reaction can be effected by combining a compound of formula IV with a compound of formula V in an inert organic reaction medium if desired in the presence of an acid acceptor such as an alkali metal carbonate and heating the resulting mixture at reflux for a period of from about 1 to about 48 hours. After this time the mixture can be filtered and distilled to yield the desired product.

The compounds of formula V when not readily available can be prepared by reacting a glycol of the formula

wherein $n$ is as heretofore described, with an aldehyde of the formula

wherein $R^4$ is as heretofore described. This reaction can be effected by combining the compounds of formulae VI and VII in an inert reaction medium such as benzene and in the presence of a catalyst such as calcium chloride or toluene-sulfonic acid. The reaction mixture can then be heated at reflux until no more water can be removed by azeotropic distillation. After this time the reaction mixture can be filtered and distilled under vacuum to yield the desired product.

Exemplary aldehydes of formula VII are formaldehyde, propionaldehyde, butyraldehyde, pentanal, hexanal, heptanal and the like.

Exemplary substituted anilines of formula IV useful in preparing the compounds of formula II are 2-methylaniline, 2-ethylaniline, 2-propylaniline, 2-isopropylaniline, 2-butylaniline, 2-hexylaniline, 2,6-dimethylaniline, 2,6-diethylaniline, 2,6-dipropylaniline, 2,6-dibutylaniline, 2,6-dihexylaniline, 2-methoxy-6-methylaniline, 2-methoxy-6-ethylaniline, 2-ethoxy-6-methylaniline, 2-ethoxy-6-ethyl-aniline, 2-propoxy-6-methylaniline, 2-butoxy-6-ethylaniline, 2-hexyloxy-6-methylaniline, 2,4,6-trimethylaniline, 2,4,6-triethylaniline, 2,4,6-tripropylaniline, 2,6-dimethyl-4-butylaniline, 2,4-dimethylaniline, 2,4-diethylaniline, 2-methyl- 4-chloroaniline, 2-methyl-3-bromoaniline, 2-methyl-4-iodoaniline, 2-methyl-4-fluoroaniline and the like.

Exemplary α-haloalkanoyl chlorides of formula III are chloroacetyl chloride, bromoacetyl chloride, iodoacetyl chloride, α-chloropropanoyl chloride, α-bromopropanoyl chloride, α-chlorobutanoyl chloride, α-chloropentanoyl chloride, α-chlorohexanoyl chloride, α-bromooctanoyl chloride and the like.

The preparation of the compounds of the present invention is more specifically illustrated in the following examples.

EXAMPLE 1

Preparation of 5-Chloromethyl-1,3-dioxolane

3-Chloropropandiol-1,2 (60 grams), paraformaldehyde (25 grams), toluenesulfonic acid (0.5 grams) and benzene (200 ml) were charged into a glass reaction vessel equipped with a mechanical stirrer, thermometer and reflux condenser with a Dean-Stark trap. The reaction mixture was heated at reflux until no more water was removed by azeotropic distillation. After this time the reaction mixture was stripped of benzene and distilled to yield the desired product 5-chloromethyl-1,3-dioxolane as an oil having a boiling point of 47° C under aspirator pressure.

EXAMPLE 2

Preparation of N-(1,3-Dioxolan-5-ylmethyl)-2,6-dimethylaniline 2,6-Dimethylaniline (94.5 grams), 5-chloromethyl-1,3-dioxolane (31.8 grams), potassium carbonate (36.7 grams) and tetraethylammonium chloride (2 grams) were charged into a glass reaction vessel equipped with a mechanical stirrer, thermometer and reflux condenser. The reaction mixture was heated at reflux for a period of 48 hours. After this time the mixture was filtered and distilled to yield the desired product N-(1,3-dioxolan-5-ylmethyl)-2,6-dimethylaniline having a boiling point of 132° C under aspirator pressure.

EXAMPLE 3

Preparation of N-(1,3-Dioxolan-5-ylmethyl)-2,6-dimethyl-α-chloroacetanilide

N-(1,3-Dioxolan-5-ylmethyl)-2,6-dimethylaniline (22.4 grams), sodium carbonate (11.5 grams), water (100 ml) and benzene (100 ml) were charged into a glass reaction vessel equipped with a mechanical stirrer and thermometer. The mixture was cooled to a temperature of about 0° C and chloroacetyl chloride (8.2 ml) was slowly added with stirring. After the addition was completed stirring was continued for a period of about one hour. The mixture was then washed with water, was dried and distilled to yield the desired product N-(1,3-dioxolan-5-ylmethyl)-2,6-dimethyl-α-chloroacetanilide as an oil boiling at 200°–205° C at 1 mm of Hg pressure.

EXAMPLE 4

Preparation of 5-β-Chloroethyl-1,3-dioxolane

4-Chlorobutandiol-1,2 (0.5 mole), paraformaldehyde (0.55 mole), toluenesulfonic acid (1 gram) and benzene (250 ml) are charged into a glass reaction vessel equipped with a mechanical stirrer, thermometer and reflux condenser with a Dean-Stark trap. The reaction mixture is heated at reflux until no more water is removed by azeotropic distillation. After this time the reaction mixture is stripped of solvent and is distilled to yield the desired product 5-β-chloroethyl-1,3-dioxolane.

EXAMPLE 5

Preparation of N-(1,3-Dioxolan-5-ylethyl)-2,6-diethylaniline 2,6-Diethylaniline (0.3 mole), 5-β-chloroethyl-1,3-dioxolane (0.3 mole), potassium carbonate (0.3 mole) and tetraethylammonium chloride (2 grams) are charged into a glass reaction vessel equipped with a mechanical stirrer, thermometer and reflux condenser. The reaction mixture is heated at reflux for a period of 4 hours. After this time the mixture is filtered to yield the desired product N-(1,3-dioxolan-5-ylethyl)-2,6-diethylaniline.

EXAMPLE 6

Preparation of N-(1,3-Dioxolan-5-ylethyl)-2,6-diethyl-α-chloroacetanilide

N-(1,3-Dioxolan-5-ylethyl)-2,6-diethylaniline (0.1 mole), sodium carbonate (0.1 mole), water (10 ml) and benzene (100 ml) are charged into a glass reaction vessel equipped with a mechanical stirrer and thermometer. The reaction mixture is cooled to a temperature of about 0° C and chloroacetyl chloride (0.11 mole) is incrementally added with stirring. After the addition is completed, stirring is continued for a period of about one hour. The mixture is then washed with water, dried over anhydrous magnesium sulfate and filtered. The filtrate is stripped of solvent and unreacted starting materials to yield the desired product N-(1,3-dioxolan-5-ylethyl)-2,6-diethyl-α-chloroacetanilide as the residue.

EXAMPLE 7

Preparation of N-(1,3-Dioxolan-5-ylmethyl)-2-methyl-6-methoxyaniline

2-Methyl-6-methoxyaniline (0.3 mole), 5-chloromethyl-1,3-dioxolane (0.3 mole), potassium carbonate (0.3 mole) and tetraethylammonium chloride (2 grams) are charged into a glass reaction vessel equipped with a mechanical stirrer, thermometer and reflux condenser. The reaction mixture is heated at reflux for a period of 4 hours. After this time the mixture is filtered and distilled to yield the desired product N-(1,3-dioxolan-5-ylmethyl)-2-methyl-6-methoxyaniline.

EXAMPLE 8

Preparation of N-(1,3-Dioxolan-5-ylmethyl)-2-methyl-6-methoxy-α-chloroacetanilide N-(1,3-Dioxolan-5-ylmethyl)-2-methyl-6-methoxyaniline (0.1 mole), sodium carbonate (0.1 mole), water (10 ml) and benzene (100 ml) are charged into a glass reaction vessel equipped with a mechanical stirrer and thermometer. The reaction mixture is cooled to a temperature of about 0° C and chloroacetyl chloride (0.11 mole) is incrementally added with stirring. After the addition is completed, stirring is continued for a period of about one hour. The mixture is then washed with water, dried over anhydrous magnesium sulfate and filtered. The filtrate is stripped of solvent and unreacted starting materials to yield the desired product N-(1,3-dioxolan-5-ylmethyl)-2-methyl-6-methoxy-α-chloroacetanilide as the residue.

EXAMPLE 9

Preparation of N-(1,3-Dioxolan-5-ylmethyl)-2-ethyl-4-chloroaniline

2-Ethyl-4-chloroaniline (0.3 mole), 5-chloromethyl-1,3-dioxolane (0.3 mole), potassium carbonate (0.3 mole) and tetraethylammonium chloride (2 grams) are charged into a glass reaction vessel equipped with a mechanical stirrer, thermometer and reflux condenser. The reaction mixture is heated at reflux for a period of 6 hours. After this time the mixture is filtered and distilled to yield the desired product N-(1,3-dioxolan-5-ylmethyl)-2-ethyl-4-chloroaniline.

EXAMPLE 10

Preparation of N-(1,3-Dioxolan-5-ylmethyl)-2-ethyl-4-chloro-α-chloroacetanilide

N-(1,3-Dioxolan-5-ylmethyl)-2-ethyl-4-chloroaniline (0.1 mole), sodium carbonate (0.1 mole), water (10 ml) and benzene (100 ml) are charged into a glass reaction vessel equipped with a mechanical stirrer and thermometer. The reaction mixture is cooled to a temperature of about 0° C and chloroacetyl chloride (0.11 mole) is incrementally added with stirring. After the addition is completed, stirring is continued for a period of about one hour. The mixture is then washed with water, dried over anhydrous magnesium sulfate and filtered. The filtrate is stripped of solvent and unreacted starting materials to yield the desired product N-(1,3-dioxolan-5-ylmethyl)-2-ethyl-4-chloro-α-chloroacetanilide as the residue.

EXAMPLE 11

Preparation of N-(1,3-Dioxolan-5-ylmethyl)-2,4,6-trimethylaniline 2,4,6-Trimethylaniline (0.3 mole), 5-chloromethyl-1,3-dioxolane (0.3 mole), potassium carbonate (0.3 mole) and tetraethylammonium chloride (2 grams) are charged into a glass reaction vessel equipped with a mechanical stirrer, thermometer and reflux condenser. The reaction mixture is heated at reflux for a period of 8 hours. After this time the mixture is filtered and distilled to yield the desired product N-(1,3-dioxolan-5-ylmethyl)-2,4,6-trimethylaniline.

EXAMPLE 12

Preparation of N-(1,3-Dioxolan-5-ylmethyl)-2,4,6-trimethyl-α-chloroacetanilide

N-(1,3-Dioxolan-5-ylmethyl)-2,4,6-trimethylaniline (0.1 mole), sodium carbonate (0.1 mole), water (10 ml) and benzene (100 ml) are charged into a glass reaction vessel equipped with a mechanical stirrer and thermometer. The reaction mixture is cooled to a temperature of about 0° C and chloroacetyl chloride (0.11 mole) is incrementally added with stirring. After the addition is completed, stirring is continued for a period of about one hour. The mixture is then washed with water, dried over anhydrous magnesium sulfate and filtered. The filtrate is stripped of solvent and unreacted starting materials to yield the desired product N-(1,3-dioxolan-5-ylmethyl)-2,4,6-trimethyl-α-chloroacetanilide as the residue.

EXAMPLE 13

Preparation of N-(1,3-Dioxolan-5-ylmethyl)-2,6-dimethyl-4-bromoaniline 2,6-Dimethyl-4-bromoaniline (0.3 mole), 5-chloromethyl-1,3-dioxolane (0.3 mole), potassium carbonate (0.3 mole) and tetraethylammonium chloride (2 grams) are charged into a glass reaction vessel equipped with a mechanical stirrer, thermometer and reflux condenser. The reaction mixture is heated at reflux for a period of 5 hours. After this time the mixture is filtered and distilled to yield the desired product N-(1,3-dioxolan-5-ylmethyl)-2,6-dimethyl-4-bromoaniline.

EXAMPLE 14

Preparation of N-(1,3-Dioxolan-5-ylmethyl)-2,6-dimethyl-4-bromo-α-chloroacetanilide N-(1,3-Dioxolan-5-ylmethyl)-2,6-dimethyl-4-bromoaniline (0.1 mole), sodium carbonate (0.1 mole), water (10 ml) and benzene (100 ml) are charged into a glass reaction vessel equipped with a mechanical stirrer and thermometer. The reaction mixture is cooled to a temperature of about 0° C and chloroacetyl chloride (0.11 mole) is incrementally added with stirring. After the addition is completed, stirring is continued for a period of about one hour. The mixture is then washed with water, dried over anhydrous magnesium sulfate and filtered. The filtrate is stripped of solvent and unreacted starting materials to yield the desired product N-(1,3-dioxolan-5-ylmethyl)-2,6-dimethyl-4-bromo-α-chloroacetanilide as the residue.

EXAMPLE 15

Preparation of 2-Methyl-5-chloromethyl-1,3-dioxolane

3-Chloropropandiol-1,2 (0.5 mole), acetaldehyde (0.5 mole), toluenesulfonic acid (0.5 grams) and benzene (200 ml) are charged into a glass reaction flask equipped with a mechanical stirrer, thermometer and reflux condenser with a Dean-Stark trap. The reaction mixture is heated at reflux until no more water is removed by azeotropic distillation. After this time the reaction mixture is stripped of solvent and is distilled to yield the desired product 2-methyl-5-chloromethyl-1,3-dioxolane.

EXAMPLE 16

Preparation of N-(2-Methyl-1,3-dioxolan-5-ylmethyl)-2-t-butylaniline 2-t-Butylaniline (0.3 mole), 2-methyl-5-chloromethyl-1,3-dioxolane (0.3 mole), potassium carbonate (0.3 mole) and tetraethylammonium chloride (2 grams) are charged into a glass reaction vessel equipped with a mechanical stirrer, thermometer and reflux condenser. The reaction mixture is heated at reflux for a period of 48 hours. After this time the mixture is filtered to yield the desired product N-2-methyl-1,3-dioxolan-5-ylmethyl)-2-t-butylaniline.

EXAMPLE 17

Preparation of
N-(2-Methyl-1,3-dioxolan-5-ylmethyl)-2-t-butyl-α-bromoacetanilide N-(2-Methyl-1,3-dioxolan-5-ylmethyl)-2-t-butylaniline (0.1 mole), sodium carbonate (0.1 mole), water (10 ml) and benzene (100 ml) are charged into a glass reaction vessel equipped with a mechanical stirrer and thermometer. The reaction mixture is cooled to a temperature of about 0° C and bromoacetyl chloride (0.11 mole) is incrementally added with stirring. After the addition is completed, stirring is continued for a period of about one hour. The mixture is then washed with water, dried over anhydrous magnesium sulfate and filtered. The filtrate is stripped of solvent and unreacted starting materials to yield the desired product N-(2-methyl-1,3-dioxolan-5-ylmethyl)-2-t-butyl-α-bromoacetanilide as the residue.

Additional exemplary compounds which can be prepared according to the procedures of the foregoing examples are N-(2-ethyl-1,3-dioxolan-5-ylmethyl)-2,6-dipropyl-α-iodoacetanilide, N-(2-propyl-1,3-dioxolan-5-ylmethyl)-2,6-dibutyl-α-fluoroacetanilide, N-(2-butyl-1,3-dioxolan-5-ylmethyl)-2,6-dihexyl-α-chloroacetanilide, N-(2-hexyl-1,3-dioxolan-5-ylmethyl)-2,6-dimethyl-α-chloroacetanilide, N-(1,3-dioxolan-5-ylmethyl)-2-ethoxy-α-chloroacetanilide, N-(1,3-dioxolan-5-ylmethyl)-2-propoxy-α-chloroacetanilide, N-(1,3-dioxolan-5-ylmethyl)-2-butoxy-α-chloroacetanilide, N-(1,3-dioxolan-5-ylmethyl)-2-pentyloxy-α-chloroacetanilide, N-(1,3-dioxolan-5-ylmethyl)-2-hexyloxy-α-chloroacetanilide, N-(1,3-dioxolan-5-ylmethyl)-2,4-diethyl-α-chloroacetanilide, N-(1,3-dioxolan-5-ylmethyl)-2-methyl-4-propyl-α-chloroacetanilide, N-(1,3-dioxolan-5-ylmethyl)-2-methoxy-4-butyl-α-chloroacetanilide, N-(1,3-dioxolan-5-ylmethyl)-2-methoxy-4-hexyl-α-chloroacetanilide, N-(1,3-dioxolan-5-ylmethyl)-2-methyl-4-iodo-α-chloroacetanilide, N-(1,3-dioxolan-5-ylmethyl)-2-methyl-4-fluoro-α-chloroacetanilide, N-(1,3-dioxolan-5-ylmethyl)-2,6-diethyl-α-chloropropionanilide, N-(1,3-dioxolan-5-ylmethyl)-N-α-chlorobutanoyl-2,6-diethylaniline, N-(1,3-dioxolan-5-ylmethyl)-N-α-bromopentanoyl-2,6-diethylaniline, N-(1,3-dioxolan-5-ylmethyl)-N-α-chlorohexanoyl-2,6-diethylaniline, N-(1,3-dioxolan-5-ylmethyl)-N-α-chloroheptanoyl-2,6-diethylaniline, N-(1,3-dioxolan-5-ylmethyl)-N-α-chlorooctanoyl-2,6-diethylaniline and the like.

For practical use as herbicides the compounds of this invention are generally incorporated into herbicidal compositions which comprise an inert carrier and a herbicidally toxic amount of such a compound. Such herbicidal compositions, which can also be called formulations, enable the active compound to be applied conveniently to the site of the weed infestation in any desired quantity. These compositions can be solids such as dusts, granules, or wettable powders; or they can be liquids such as solutions, aerosols, or emulsifiable concentrates.

For example, dusts can be prepared by grinding and blending the active compound with a solid inert carrier such as the talcs, clays, silicas, pyrophyllite, and the like. Granular formulations can be prepared by impregnating the compound, usually dissolved in a suitable solvent, onto and into granulated carriers such as the attapulgites or the vermiculites, usually of a particle size range of from about 0.3 to 1.5 mm. Wettable powders, which can be dispersed in water or oil to any desired concentration of the active compound, can be prepared by incorporating wetting agents into concentrated dust compositions.

In some cases the active compounds are sufficiently soluble in common organic solvents such as kerosene or xylene so that they can be used directly as solutions in these solvents. Frequently, solutions of herbicides can be dispersed under super-atmospheric pressure as aerosols. However, preferred liquid herbicidal compositions are emulsifiable concentrates, which comprise an active compound according to this invention and as the inert carrier, a solvent and an emulsifier. Such emulsifiable concentrates can be extended with water and/or oil to any desired concentration of active compound for application as sprays to the site of the weed infestation. The emulsifiers most commonly used in these concentrates are nonionic or mixtures of nonionic with anionic surface-active agents. With the use of some emulsifier systems an inverted emulsion (water in oil) can be prepared for direct application to weed infestations.

A typical herbicidal composition according to this invention is illustrated by the following example, in which the quantities are in parts by weight.

Example 18

| Preparation of a Dust | |
|---|---|
| Product of Example 3 | 10 |
| Powdered Talc | 90 |

The above ingredients are mixed in a mechanical grinder-blender and are ground until a homogeneous, free-flowing dust of the desired particle size is obtained. This dust is suitable for direct application to the site of the weed infestation.

The compounds of this invention can be applied as herbicides in any manner recognized by the art. One method for the control of weeds comprises contacting the locus of said weeds with a herbicidal composition comprising an inert carrier and as an essential active ingredient, in a quantity which is herbicidally toxic to said weeds, a compound of the present invention. The concentration of the new compounds of this invention in the herbicidal compositions will vary greatly with the type of formulation and the purpose for which it is designed, but generally the herbicidal compositions will comprise from about 0.05 to about 95 percent by weight of the active compounds of this invention. In a preferred embodiment of this invention, the herbicidal compositions will comprise from about 5 to about 75 percent by weight of the active compound. The compositions can also comprise such additional substances as other pesticides, such as insecticides, nematocides, fungicides, and the like; stabilizers, spreaders, deactivators, adhesives, stickers, fertilizers, activators, synergists, and the like.

The compounds of the present invention are also useful when combined with other herbicides and/or defoliants, dessicants, growth inhibitors, and the like in the herbicidal compositions heretofore described. These other materials can comprise from about 5% to about 95% of the active ingredients in the herbicidal compositions. Use of combinations of these other herbicides and/or defoliants, dessicants, etc. with the compounds of the present invention provide herbicidal compositions which are more effective in controlling weeds and often provide results unattainable with separate compositions of the individual herbicides. The other herbicides, defoliants, dessicants and plant growth inhibitors, with which the compounds of this invention can be used in the herbicidal compositions to control weeds, can include chlorophenoxy herbicides such as 2,4-D, 2,4,5-T, MCPA, MCPB, 4(2,4-DB), 2,4-DEB, 4-CPB, 4-CPA, 4-CPP, 2,4,5-TB, 2,4,5-TES, 3,4-DA, silvex and the like; carbamate herbicides such as IPC, CIPC, swep, barban, BCPC, CEPC, CPPC, and the like; thiocarbamate and dithiocarbamate herbicides such as CDEC, metham sodium, EPTC, diallate, PEBC, perbulate, vernolate and the like; substituted urea herbicides such as norea, siduron, dichloral urea, chloroxuron, cycluron, fenuron, monuron, monuron TCA, diuron, linuron, monolinuron, neburon, buturon, trimeturon and the like; symmetrical triazine herbicides such as simazine, chlorazine, atraone, desmetryne, norazine, ipazine, prometryn, atazine, trietazine, simetone, prometone, propazine, ametryne and the like; chloroacetamide herbicides such as 4-(chloroacetyl)morpholine, 1-(chloroacetyl)piperidine and the like; chlorinated aliphatic acid herbicides such as TCA, dalapon, 2,3-dichloropropionic acid, 2,2,3-TPA and the like; chlorinated benzoic acid and phenylacetic acid herbicides such as 2,3,6-TBA, 2,3,5,6-TBA, dicamba, tricamba, amiben, fenac, PBA, 2-methoxy-3,6-dichlorophenylacetic acid, 3-methoxy-2,6-dichlorophenylacetic acid, 2-methoxy-3,5,6-trichlorophenylacetic acid, 2,4-dichloro-3-nitrobenzoic acid and the like; and such compounds as aminotriazole, maleic hydrazide, phenyl mercuric acetate, endothal, biuret, technical chlordane, dimethyl 2,3,5,6-tetrachloroterephthalate, diquat, erbon, DNC, DNBP, dichlobenil, DPA, diphenamid, dipropalin, trifluralin, solan, dicryl, merphos, DMPA, DSMA, MSMA, potassium azide, acrolein, benefin, bensulide, AMS, bromacil, 2-(3,4-dichlorophenyl)-4-methyl-1,2,4-oxadiazolidine-3,5-dione, bromoxynil, cacodylic acid, CMA, CPMF, cypromid, DCB, DCPA, dichlone, diphenatril, DMTT, DNAP, EBEP, EXD, HCA, ioxynil, IPX, isocil, potassium cyanate, MAA, MAMA, MCPES, MCPP, MH, molinate, NPA, OCH, paraquat, PCP, picloram, DPA, PCA, pyrichlor, sesone, terbacil, terbutol, TCBA, brominil, CP-50144, H-176-1, H-732, M-2901, planavin, sodium tetraborate, calcium cyanamid, DEF, ethyl xanthogen disulfide, sindone, sindone B, propanil and the like.

Such herbicides can also be used in the methods and compositions of this invention in the form of their salts, esters, amides, and other derivatives whenever applicable to the particular parent compounds.

Weeds are undesirable plants growing where they are not wanted, having no economic value, and interfering with the production of cultivated crops, with the growing of ornamental plants, or with the welfare of livestock. Many types of weeds are known, including annuals such as pigweed, lambsquarters, foxtail, crabgrass, wild mustard, field pennycress, ryegrass, goose grass, chickweed, wild oats, velvet-leaf, purslane, barnyardgrass, smartweed, knotweed, cocklebur, wild buckwheat, kochia, medic, corn cockle, ragweed, sow-thistle, coffeeweed, croton, cuphea, dodder, fumitory, groundsel, hemp nettle, knawel, spurge, spurry, emex, jungle rice, pondweed, dog fennel, carpetweed, morningglory, bedstraw, ducksalad, naiad, cheatgrass, fall panicum, jimsonweed, witchgrass, switchgrass, watergrass, teaweed, wild turnip and sprangletop; biennials such as wild carrot, matricaria, wild barley, campion, chamomile, burdock, mullein, roundleaved mallow, bull thistle, hounds-tongue, moth mullein and purple star thistle; or perennials such as white cockle, perennial ryegrass, quackgrass, Johnson grass, Canada thistle, hedge bindweed, Bermuda grass, sheep sorrel, curly dock, nutgrass, field chickweed, dandelion, campanula, field bindweed, Russian knapweed, mesquite, toadflax, yarrow, aster, gromwell, horsetail, ironweed, sesbania, bulrush, cattail, wintercress, horsenettle, nutsedge, milkweed and sicklepod.

Similarly, such weeds can be classified as broadleaf or grassy weeds. It is economically desirable to control the growth of such weeds without damaging beneficial plants or livestock.

The new compounds of this invention are particularly valuable for weed control because they are toxic to many species and groups of weeds while they are relatively nontoxic to many beneficial plants. The exact amount of compound required will depend on a variety of factors, including the hardiness of the particular weed species, weather, type of soil, method of application, the kind of beneficial plants in the same area, and the like. Thus, while the application of up to only about one or two ounces of active compound per acre may be sufficient for good control of a light infestation of weeds growing under adverse conditions, the application of ten pounds or more of an active compound per acre may be required for good control of a dense infestation of hardy perennial weeds growing under favorable conditions.

The herbicidal toxicity of the new compounds of this invention can be illustrated by many of the established testing techniques known to the art, such as pre- and post- emergence testing.

The herbicidal activity of the compounds of this invention was demonstrated by an experiment carried out for the pre-emergence control of a variety of weeds. In this experiment small plastic greenhouse pots filled with dry soil were seeded with the various weed seeds. Twenty-four hours or less after seeding the pots were sprayed with water until the soil was wet and the test compound formulated as an aqueous emulsion of an acetone solution containing emulsifiers was sprayed at the indicated concentration on the surface of the soil.

After spraying, the soil containers were placed in the greenhouse and provided with supplementary heat as required and daily or more frequent watering. The plants were maintained under these conditions for a period of from 15 to 21 days, at which time the condition of the plants and the degree of injury to the plants was rated on a scale of from 0 to 10, as follows: 0 = no injury, 1,2 = slight injury, 3,4 = moderate injury, 5,6 = moderately severe injury 7,8,9 = severe injury and 10 = death. The effectiveness of this compound is demonstrated by the following data:

TABLE I

| Weed Species | Injury Rating Product of Example 3 Concentration (lbs/acre) 10 |
|---|---|
| Yellow Nutsedge | 10 |
| Wild Oats | 7 |
| Jimsonweed | 6 |
| Velvetleaf | 1 |
| Johnson Grass | 7 |
| Pigweed | 10 |

TABLE I-continued

| Weed Species | Injury Rating Product of Example 3 Concentration (lbs/acre) 10 |
|---|---|
| Mustard | 5 |
| Yellow Foxtail | 10 |
| Barnyardgrass | 10 |
| Crabgrass | 10 |
| Cheatgrass | 10 |
| Morningglory | 4 |

The herbicidal activity of the compounds of this invention was also demonstrated by an experiment carried out for the post-emergence control of a variety of weeds. In this experiment the compound to be tested was formulated as an aqueous emulsion and sprayed at the indicated dosage on the foliage of the weeds that have attained a prescribed size. After spraying the plants were placed in a greenhouse and watered daily or more frequently. Water was not applied to the foliage of the treated plants. The severity of the injury was determined 10 to 15 days after treatment and was rated on the scale of from 0 to 10 heretofore described. The effectiveness of this compound is demonstrated by the following data:

TABLE II

| Weed Species | Injury Rating Product of Example 3 Concentration (lbs/acre) 10 |
|---|---|
| Yellow Nutsedge | 9 |
| Wild Oats | 7 |
| Jimsonweed | 5 |
| Johnson Grass | 8 |
| Pigweed | 10 |
| Mustard | 10 |
| Yellow Foxtail | 8 |
| Barnyardgrass | 9 |
| Crabgrass | 7 |
| Morningglory | 3 |
| Bindweed | 5 |

We claim:

1. A herbicidal composition comprising an inert carrier and, as an essential active ingredient, in a quantity toxic to weeds, a compound of the formula

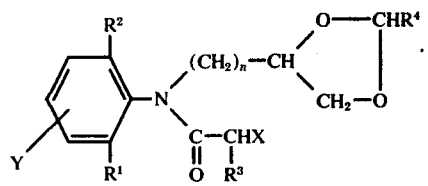

wherein Y is selected from the group consisting of hydrogen, lower alkyl and halogen, $R^1$ is selected from the group consisting of hydrogen, lower alkyl and lower alkoxy; $R^2$ is lower alkyl; $R^3$ and $R^4$ are independently selected from the group consisting of hydrogen and lower alkyl; X is halogen; and n is the integer 1 or 2.

2. The herbicidal composition of claim 1 wherein the compound is N-(1,3-dioxolan-5-ylmethyl)-2,6-dimethyl-α-chloroacetanilide.

3. The herbicidal composition of claim 1 wherein the compound is N-(1,3-dioxolan-5-ylethyl)-2,6-diethyl-α-chloroacetanilide.

4. The herbicidal composition of claim 1 wherein the compound is N-(1,3-dioxolan-5-ylmethyl)-2-methyl-6-methoxy-α-chloroacetanilide.

5. The herbicidal composition of claim 1 wherein the compound is N-(1,3-dioxolan-5-ylmethyl)-2-ethyl-4-chloro-α-chloroacetanilide.

6. The herbicidal composition of claim 1 wherein the compound is N-(1,3-dioxolan-5-ylmethyl)-2,4,6-trimethyl-α-chloroacetanilide.

7. The herbicidal composition of claim 1 wherein the compound is N-(1,3-dioxolan-5-ylmethyl)-2,6-dimethyl-4-bromo-α-chloroacetanilide.

8. The herbicidal composition of claim 1 wherein the compound is N-(2-methyl-1,3-dioxolan-5-ylmethyl)-2-t-butyl-α-bromoacetanilide.

9. A method of controlling weeds which comprises contacting said weeds with a herbicidally effective amount of a herbicidal composition of claim 1.

* * * * *